United States Patent [19]

Amato et al.

[11] Patent Number: 4,508,921

[45] Date of Patent: Apr. 2, 1985

[54] PROCESS FOR PREPARATION OF ALPHA-ALKYL AMINO ACIDS

[75] Inventors: Joseph S. Amato, Brooklyn, N.Y.; Leonard M. Weinstock, Belle Mead; Sandor Karady, Mountainside, both of N.J.

[73] Assignee: Merck & Co., Inc., Rahway, N.J.

[21] Appl. No.: 625,761

[22] Filed: Jun. 28, 1984

[51] Int. Cl.³ .............................................. C07C 51/09
[52] U.S. Cl. ..................................... 562/443; 548/228; 548/496; 562/445; 562/446; 562/561; 562/567; 562/574; 562/575
[58] Field of Search ............... 562/443, 445, 446, 561, 562/567, 574, 575; 548/496

[56] References Cited

U.S. PATENT DOCUMENTS

| | | | |
|---|---|---|---|
| 3,422,135 | 1/1969 | Yamada | 562/575 |
| 4,264,771 | 4/1981 | Steglich | 562/575 |
| 4,339,589 | 7/1982 | Steglich | 562/575 |

OTHER PUBLICATIONS

Greenstein, "Chemistry of the Amino Acids," vol. 3, p. 2559–2579, (1961).

Primary Examiner—Michael L. Shippen
Attorney, Agent, or Firm—Alice O. Robertson; Michael C. Sudol; Mario A. Monaco

[57] ABSTRACT

A process for preparing α-alkyl amino acids by enantioretentive α-alkylation of α-amino acids is described. The products are bioactive compounds including some useful as therapeutic agents.

3 Claims, No Drawings

PROCESS FOR PREPARATION OF ALPHA-ALKYL AMINO ACIDS

The present invention is directed to a process for the preparation of α-alkyl amino acids, more particularly, to a process for their preparation by enantioretentive alkylation of optically active α-amino acids.

BACKGROUND OF THE INVENTION

Naturally occurring amino acids include hydrolysis products of proteins and components of antibiotics and other microbiological metabolic products. These naturally occurring amino acids exist in enantiomeric forms. It has been found that a number of α-alkyl analogs when of the same enantiomeric configuration have the property of altering the metabolic path normally taken, producing results which are adaptable to being used to therapeutic advantage both directly as therapeutic agents and indirectly as agents for study of biological functions leading to means for therapeutic methods. Thus, for example, methyldopa, L-α-methyl-3,4-dihydroxyphenylalanine, inhibits the decarboxylation of dopa and 5-hydroxytryptophan, thereby decreasing the concentration of 5-hydroxytryptamine, dopamine and norepinephrine in the central nervous system. This metabolic behavior manifests itself, in a hypotensive effect which has been utilized therapeutically in a well-known antihypertensive drug, methyldopa. Other α-alkyl amino acids with the same enantiomeric configuration as those of the naturally occurring amino acids have been found also to be inhibitors of certain functions of amino acids and useful at the very least for the study of metabolic inhibition and metabolic pathways. Thus, L-(−)-α-methylphenylalanine has been reported to be tyrosine hydroxylase inhibitor (Bollinger, F. W., J. Med. Chem., 14, 373 (1971) and U.S. Pat. No. 3,758,559) and to have properties that make it more useful for treatment of heart condition than L-(−)-α-methyltyrosine because it has less of a tendency to cause drowsiness and mental depression. The preparation and utilization of α-methylphenylalanine for the synthesis of antimitotic peptides which may be ultimately useful for inhibition of cancerous tumor growth is reported in C.R. Acad. Sc. Paris, 268, 307. The resistance of peptides containing α-methylamino acids to the action of proteolytic enzymes are noted in F. Turk et al., Molecular Pharmacology, 12, 217–224 (1976). Thus, α-alkyl analogs of naturally occurring amino acids are of useful therapeutic and biological applications.

In all of the foregoing, the α-alkyl analog is in an enantiomeric configuration corresponding to that of the non-alkylated amino acid. The customary method for obtaining enantiomers has been to prepare the racemic compound and then to subject the racemic compound to resolution. A method which would permit entry of an alkyl group into an optically active α-amino acid to produce an α-alkyl amino acid of the same enantiomeric configuration, i.e., an enantioretentive process, would be highly desirable. In the literature, there has been reported a method for alkylating an enantiomer with retention of configuration which has been successful with proline but it has not been successful with the acyclic amino acids, i.e., amino acids in which the α-amino nitrogen is not part of a cyclic system. Since amino acids other than proline and hydroxyproline are acyclic at the α-amino position, there is still a need for a process whereby amino acids may be alkylated with retention of configuration when the amino acid is acyclic.

STATEMENT OF THE INVENTION

According to the present invention it has been discovered that an optically active acyclic or open chain α-alkyl-α-amino acid may be prepared from the corresponding optically active acyclic α-amino acid by a process which comprises:

(1) converting an optically active acyclic α-amino acid to a 2-aryloxazolidinone compound in which the non-hydrogen substituent at the 4-position and the aryl group at the 2-position are in a cis relationship, by (a) reacting an optically active nitrogen protected α-amino acid with an aromatic aldehyde in the presence of an acid catalyst, or (b) reacting an optically active unprotected amino acid with an aromatic aldehyde in alkaline, preferably ethanolic solution to produce a Schiff base of the amino acid salt, and thereafter reacting the Schiff base with an acylating agent, (2) stereospecifically alkylating said 2-aryloxazolidinone compound by first forming an alkali metal enolate by reacting the oxazolidinone compound with a strong base at greatly reduced temperatures followed by reacting the enolate with an alkylating agent, and (3) generating the α-alkyl-α-amino acid from the alkylated 2-aryloxazolidinone by alkaline hydrolysis to open of the ring followed by hydrolytic or reductive removal of the protective group.

The process can be seen schematically as follows:

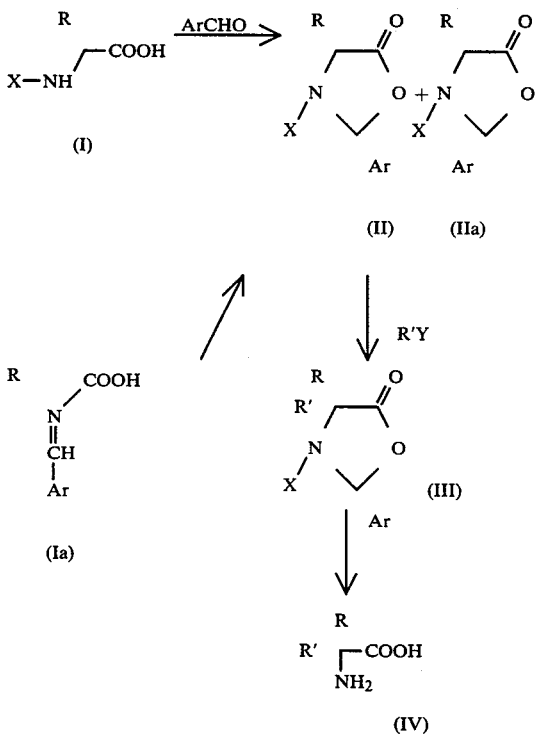

In the foregoing formulas, R is a residue of a acyclic α-amino acid, R' is an alkyl group as hereinafter defined, X is a protecting group for the amino nitrogen, and Y is a residue of an alkylating agent.

The expression "acyclic α-amino acids" as herein employed is intended to embrace those optically active amino acids in which the α-amino group is not part of a ring. All amino acids will therefore contain the following open chain configuration:

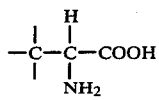

It is contemplated that one of the bonds attached to the β-carbon atom may be attached to a carbocyclic group. Thus, amino acids containing a carbocyclic group such as phenylalanine, tyrosine and 3-hydroxytyrosine are within the contemplation of "acyclic amino acids" as herein employed.

Moreover, since the invention is directed to optically active amino acids, glycine is not within the contemplation of the present invention. By "alkyl" is meant not only lower alkyl from 1 to about 6 carbon atoms but also alkyl substituted with halo, alkoxy, and/or aryl. Thus, it is intended to include not only methyl, ethyl, propyl and the like but also benzyl, 2-phenylethyl, fluoromethyl, chloromethyl, methoxymethyl, 2-methoxyethyl, ethoxymethyl, and the like.

In the specification and claims, the designation "cis" or "trans" is employed to designate the relationship between the group in the 4-position and the aryl in the 2-position of the oxazolidinone ring. When the non-hydrogen group attached to the α-carbon of the amino acid is, on the formation of the oxazolidinone, in a cis relationship to the aryl group, the oxazolidinone compound is designated "cis". It has been established earlier that the major oxazolidinone formed from amino acids is in a cis relationship (Freidinger et al., J. Org. Chem., 48, 77 (1983)). In the above reaction scheme, Formula II represents the cis oxazolidinone compound and Formula IIa the trans.

In the first step of the process, namely the preparation of the oxazolidinone compound, one method contemplates use of the amino acid as a protected amino acid. By "protected amino acid" is meant an amino acid in which the amino nitrogen is protected from undesirable side reactions by the introduction of a group which is capable of being facilely and selectively removed. With aliphatic hydroxylated amino acids such as serine or threonine, the hydroxyl group as well as the amino group should be protected. Suitable protecting groups include carbobenzyloxy (frequently termed "carbobenzoxy"), carbo-tert-butyloxy (or tert-butyloxycarbonyl), trifluoroacetyl, and the like. Other protective groups may be found listed on pages 160–161 of R. A. Boissonnas, Adv. Org. Chem. 3, 159 (1963). For ease of recovery and for the obtaining of good yields of the final product, the carbobenzyloxy group is the preferred protecting group. The protected amino acid may be prepared by procedures well known in the art and which are summarized in the aforecited reference and/or which are hereinafter described.

The aromatic aldehyde to be reacted with the protected amino acid may be any of a number of aldehydes. Suitable aldehydes include benzaldehyde, 2,6-dichlorobenzaldehyde, m-tolualdehyde, p-tolualdehyde, o-chlorobenzaldehyde, m-nitrobenzaldehyde, salicylaldehyde and the like.

The acid catalyst for the oxazolidinone formation may be any of the conventional strong acid condensation catalysts such as p-toluenesulfonic acid, trifluoroacetic acid, sulfuric acid, benzenesulfonic acid, dinitrobenzoic acid, and the like.

In the reaction, the aldehyde is employed in excess, usually from about two to six fold molar excess based on the amino acid. The acid condensation catalyst is employed in substantially equimolar amounts to the amount of amino acid.

In carrying out the first step of the synthesis employing an N-protected acyclic α-amino acid, the protected amino acid, an aromatic aldehyde and an acid catalyst are heated together in an inert solvent whereupon a reaction takes place with the formation of an oxazolidinone compound and water of reaction which is azeotropically removed and whereby there is recovered a mixture of a major amount of cis 2-aryl-3-(N-protecting substituent)-oxazolidinone intermediate compound (II) and a minor amount of the corresponding trans compound (IIa).

In an alternative method for carrying out the preparation of the cis oxazolidinone compound, an unprotected acyclic α-amino acid and aromatic aldehyde are reacted together under alkaline conditions to obtain a Schiff base of an alkali-metal salt of the α-amino acid, and then, the Schiff base is caused to react with carbobenzyloxy chloride by intimately contacting the reactants for at least several hours to obtain a mixture of cis (II) and trans (IIa) 2-aryloxazolidinone compounds. This method is not suitable when the amino acid is an aliphatic hydroxy amino acid since it would be necessary to protect the hydroxy group during the preparation of the Schiff base. Thus, the first method would be employed for hydroxy amino acids.

The aromatic aldehydes which may be employed to prepare the Schiff base are the same as those previously detailed as being appropriate for reacting with the protected amino acid to produce the oxazolidinone compounds.

The reaction mixture containing the cis and the trans isomers obtained by either method may be subjected to conventional separation and purification procedures. Usually, one of the isomers is obtained in crystalline form. In the present process, the desired cis isomer is not only the major product but generally also is obtained in a crystalline form and so may be recovered by filtration and thereafter used in the next step with or without purification. Alternatively, a chromatographic procedure utilizing adsorbent on a column may be employed to separate the isomers. When this method is employed, the mixture is placed on an adsorbent and subjected to action of an eluting agent to separate the isomers and to recover a substantially pure 2-aryl-3-(N-protecting substituent)oxazolidinone intermediate compound from the eluate fractions after evaporating off the solvent from the eluate. The intermediate compound then may be crystallized or recrystallized.

For the chromatographic separation of the cis and trans oxazolidinone compounds, any of the conventional adsorbents may be employed. Suitable adsorbents include silica gel, alumina, chemically modified dextran obtainable under the trade name Sephadex, and the like. The separation may be carried out on a column with or without pressure. If small amounts of product are desired, a thin layer chromatographic method also may be employed. A preferred adsorbent is silica gel for which the preferred eluants are mixtures of aliphatic and halogenated hydrocarbon solvents. Thus, for example, mixtures of hexane and methylene chloride in various ratios have been effective.

For alkylating the 2-aryl-3-(N-protecting substituent)oxazolidinone intermediate compound, the oxazolidinone compound is first converted to its alkali metal enolate. The preparation of the enolate is carried out by adding a strong base with stirring to a solution of the oxazolidinone compound in an inert solvent at temperatures below about −50° C., preferably −70° to −78° C. After completion of the addition, stirring is continued for a short period to complete the formation of the alkali metal enolate of the 2-aryl-3-(N-protecting substituent)oxazolidinone compound. To the resulting solution, while still maintaining the reaction mixture at the reduced temperatures, an alkylating agent is added in a portionwise manner. After completion of the addition, the mixture is allowed to warm slowly to 0° C. and then maintained at this temperature from a few minutes to a few hours to complete the alkylation with the formation of 4-alkyl-2-aryl-3-(N-protecting substituent)-oxazolidinone compound in which the entering alkyl group replaces the hydrogen at the 4-position in a manner which retains the enantiomer configuration. Thus, as can be seen in Formula III, the alkyl group, R' is in a trans relationship. The reaction mixture then is allowed to warm to room temperature and is recovered by conventional procedures such as by adding a water-immiscible organic solvent to the reaction mixture to dissolve the alkylated oxazolidone compound, washing the organic solution with saturated sodium chloride solution, drying, and subjecting the dried solution to reduced pressure to obtain as residue the 4-alkylated-2-aryl-3-(N-protecting group)oxazolidinone compound (III). The alkylated compound then may be purified in a conventional manner such as preparative chromatography using adsorbents previously detailed or crystallization.

For preparing the alkali metal enolate, any strong base may be employed. Suitable bases include potassium hexamethyldisilazane, lithium diisopropylamide, potassium diisopropylamide, potassium methylsulfinylmethylide, lithium 1-(dimethylamino)naphthalenide, lithium L-$\alpha,\alpha'$-dimethylbenzylamide, sodium hydride and the like.

An ethereal solvent is preferably employed for carrying out the reaction for the preparation of the alkali metal enolate and the subsequent alkylation step. A preferred solvent is tetrahydrofuran, although dioxane, diisopropyl ether, diethyl ether and the like may be employed.

In the foregoing alkylation, substantially equimolar amounts of the reactants are employed although a slight excess of the alkylating agent may be employed.

For introducing the alkyl group, any suitable alkylating agent may be employed. Suitable agents include alkyl halides, alkyl sulfates, alkyl methanesulfonates and the like. In view of the fact that "alkyl" is intended to embrace substituted alkyl particularly aryl-, alkoxy-, or halo-substituted alkyl such as benzyl, 2-methoxyethyl, or fluoromethyl, the term "alkyl" in the alkylating agent also embraces substituted alkyl halides, sulfates, methanesulfonates and the like.

The alkylated oxazolidinone compound may be converted to the desired $\alpha$-alkyl-acyclic $\alpha$-amino acid by an alkaline hydrolysis reaction to open the ring followed by a reaction to remove the protecting group. The method for removing protecting group varies with the group to be removed. Thus, a suitable method for a particular group may be hydrogenolysis and/or acid hydrolysis and/or a special method. Hydrogenolysis is preferred as a method providing more efficient reaction and cleaner products. Thus, preferred protecting groups are those which may be removed by hydrogenolysis rather than by chemical methods.

In carrying out the ring opening hydrolysis, the alkylated-oxazolidinone compound and dilute alkali are intimately contacted in an appropriate solvent medium. Dilute aqueous alkali hydroxide or other strong base, and polar solvent such as methanol, ethanol, isopropanol and the like are suitable. The reaction may be carried out by heating the mixture at reflux temperature where it proceeds readily with the formation of an $\alpha$-alkyl-N-protected acyclic amino acid compound and the regeneration of the aromatic aldehyde which may be codistilled with water leaving an $\alpha$-alkyl-N-protected acyclic amino acid compound (i.e., an alkali metal salt of the amino acid).

The hydrogenolysis of the protecting group from the amino acid compound, thus obtained, may be carried out by mixing together the amino acid compound, catalyst and solvent and subjecting the mixture to hydrogen at elevated pressures. The pressures employed depend on the catalyst employed; thus, they may be several pounds per square inch (psi) with noble metal catalysts to very high pressures with other metal catalysts. Suitable catalysts include platinum-carbon, palladium-carbon, palladium on barium sulfate, nickel-chromium, Raney nickel, ruthenium-silica, platinum-silica, iridium-silica, copper-chromium oxide and the like.

After completion of the hydrogenation, the product may be recovered by filtering off the catalyst, concentrating the filtrate to obtain the desired optically active acyclic $\alpha$-alkyl-$\alpha$-amino acid product of the same enantiomeric configuration as the unalkylated amino acid.

If acid hydrolysis is selected as a method for removing the protecting group, the reaction may be carried out by heating the amino acid compound obtained in the ring-opening alkaline hydrolysis with an acid such as, for example, 6N hydrochloric acid under reflux for several hours to obtain the desired optically active acyclic $\alpha$-alkyl-$\alpha$-amino acid product, and therfter, isolating the product from the reaction mixture by conventional procedures.

A preferred method for carrying out the invention for the preparation of an optically active acyclic $\alpha$-alkyl-$\alpha$-amino acid from the corresponding optically active non-alkylated amino acid comprises:

(1) heating together a N-carbobenzyloxylated optically active acyclic $\alpha$-amino acid and an aromatic aldehyde in the presence of a strong dehydrating acid in an inert solvent with azeotropic removal of water by-product to obtain a mixture of cis and trans isomers of 2-aryl-3-carbobenzyloxyoxazolidinone intermediate, (2) applying the mixture to an adsorbent bed and eluting with organic hydrocarbon solvent mixtures to separate the isomers and to recover in substantially pure form cis-2-aryl-3-carbobenzyloxyoxazolidinone intermediate, (3) intimately contacting said oxazolidinone compound with a strong alkali metal base in an inert solvent medium at temperatures in the range −70° to −78° C. to obtain an alkali metal enolate of said oxazolidinone compound, (4) adding portionwise an alkylating agent to the cooled solution of the alkali metal enolate of the oxazolidinone compound, then gradually allowing the temperature to rise to 0° C. to obtain a cis-4-alkyl-2-aryl-3-carbobenzyloxyoxazolidinone intermediate, and recovering the intermediate from the reaction mixture, (5) intimately contacting said 4-alkyl-2-aryl-3-carbobenzyloxyoxazolidinone intermediate with a dilute alcoholic solution of base to obtain a cis-α-alkyl-N-carbobenzyloxy-acyclic-α-amino acid compound and recovering the acid compound from the reaction mixture, (6) subjecting an alcoholic solution of the recovered amino acid compound to hydrogen at elevated pressures to reductively remove the carbobenzyloxy protecting group to obtain the desired α-alkyl-α-amino acid having the same enantiomeric configuration as that of the starting unalkylated α-amino acid.

In one preferred method, the separation of the mixtures according to step (2) is carried out by applying the mixture to an adsorbent bed and eluting with organic hydrocarbon solvent mixtures.

The alkylated amino acids which correspond to an unnatural configuration of amino acids may be prepared, if desired, by alkylating the trans oxazolidinone compound (the minor component) or by starting with the unnatural amino acid. In the case of phenylalanine, α-methylphenylalanine corresponding to the unnatural configuration may be obtained by employing natural alanine as starting material, and then alkylating the cis-oxazolidinone compound with benzyl bromide to obtain the (R)-α-methylphenylalanine.

The following examples illustrate the invention but are not to be construed as limiting:

EXAMPLE 1

Preparation of cis-4-benzyl-3-carbobenzyloxy-2-phenyloxazolidinone 8 grams (25 millimoles) of (S)-N-carbobenzyloxyphenylalanine, 35 milliliters (150 millimoles) of benzaldehyde, 4.75 grams (25 millimoles) of p-toluene-sulfonic acid hydrate and about 200 milliliters of toluene were mixed together and heated at reflux temperature in a water separator over a three-hour period, during which time a reaction took place with the formation of a 4-benzyl-3-carbobenzyloxy-2-phenyloxazolidinone compound which remained in the reaction mixture and water by-product which was azeotropically distilled. After completion of the heating, the organic reaction mixture was allowed to cool to room temperature, washed twice with 1N sodium bicarbonate solution, and concentrated under reduced pressure to obtain crude 4-benzyl-3-carbobenzyloxy-2-phenyloxazolidinone compound as an oil. The latter was purified by adding 250 milliliters of half-saturated sodium bisulfite solution, allowing the resulting mixture to stand at room temperature for about 10 minutes to obtain an addition product of unreacted benzaldehyde, and then removing the addition product by filtration. The aqueous filtrate was extracted twice with methylene chloride. The methylene chloride solution was concentrated in vacuo, petroleum ether added thereto to wash the gum residue and the ether then decanted to recover 8 grams of residue. An H 'NMR analysis indicated the gum was cis-4-benzyl-3-carbobenzyloxy-2-phenyloxazolidinone. The gum was stirred with ether to form crystals which were recovered by filtration. The crystals amounted to 2 grams of the desired cis-4-benzyl-3-carbobenzyloxy-2-phenyloxazolidinone compound, m.p. 109°–112° C.

EXAMPLE 2

Preparation of (S)-(α-Methyl)phenylalanine from (S)-Phenylalanine cis-4-Benzyl-3-carbobenzyloxy-2-phenyloxazolidinone. 16 grams (50 millimoles) of (S)-N-carbobenzyloxyphenylalanine, 70 milliliters (300 millimoles) of benzaldehyde and 9.5 grams (50 millimoles) of p-toluenesulfonic acid hydrate and about 200 milliliters of 1,1,1-trichloroethane were mixed together and heated at reflux temperature in a water separator over a five hour period during which time a reaction took place with the formation of a 4-benzyl-2-phenyl-3-carbobenzyloxyoxazolidinone compound, which remained in the reaction mixture and water by-product which was azeotropically distilled. The mixture then was allowed to cool to room temperature and washed twice with sodium bicarbonate solution. The organic solution was dried with magnesium sulfate, the drying agent then removed, and the dried solution concentrated under reduced pressure to obtain the oxazolidinone compound as an oil. 100 milliliters of diethyl ether was added to the oil and seeded with 50 milligrams of a sample of 4-benzyl-3-carbobenzyloxy-2-phenyloxazolidinone compound previously prepared as described in Example 1, whereupon crystals separated. The crystals were recovered by filtration, washed with diethyl ether and air-dried to constant weight to obtain 4.1 grams of a cis-4-benzyl-3-carbobenzyloxy-2-phenyloxazolidinone compound of melting point 113°–116° C. A second crop of 4.3 grams was obtained, amounting to a total yield of 8.4 grams or 44 percent of theoretical.

4-Benzyl-3-carbobenzyloxy-4-methyl-2-phenyloxazolidinone. 1.1 grams (3 millimoles) of the 4-benzyl-3-carbobenzyloxy-2-phenyloxazolidinone above-prepared was dissolved in 30 milliliters of tetrahydrofuran and cooled to −78° C. To this solution was added 5 milliliters of 0.6 molar solution of potassium hexamethyldisilazane in toluene to form the potassium enolate of 4-benzyl-3-carbobenzoxy-2-phenyloxazolidinone; after about 5 minutes, 170 microliters (3 millimoles) of methyl iodide was added, the mixture allowed to warm to 0° C. and maintained at 0° C. for about 30 minutes. The mixture then was partitioned between aqueous phosphate buffer of pH 7 and methylene chloride. The organic solution was washed with saturated sodium chloride solution, dried over magnesium sulfate and concentrated under reduced pressure to obtain a residue comprising crude 4-benzyl-3-carbobenzyloxy-4-methyl-2-phenyloxazolidinone intermediate product. The crude methylated oxazolidinone product was subjected to low pressure (10 psi) chromatographic purification on silica gel employing 30% hexane:70% methylene chloride as eluant to obtain 400 milligrams of semi-crystalline 4-benzyl-3-carbobenzyloxy-4-methyl-2-phenyloxazolidinone compound wherein the entering methyl group is trans to the benzyl and phenyl.

(S)-α-methylphenylalanine. The cis-4-benzyl-3-carbobenzyloxy-4-methyl-2-phenyloxazolidinone compound thus obtained (400 milligrams; 1 millimole) was dissolved in 5 milliliters of methanol and 5 milliliters of 1N sodium hydroxide solution and the resulting solution heated at reflux temperature for about one hour to hydrolyze the oxazolidinone and to obtain (S)-N-carbobenzyloxy-(α-methyl)phenylalanine compound. The hydrolysis mixture was heated with water to remove benzaldehyde from the reaction mixture by codistilling with water. The remaining solution was extracted three times with methylene chloride, the methylene chloride extracts combined, dried over magnesium sulfate, then the drying agent filtered and the filtrate concentrated in vacuo to obtain 300 milligrams of (S)-N-carbobenzyloxy-(α-methyl)phenylalanine.

200 milligrams (0.64 millimole) of (S)-N-carbobenzyloxy(α-methyl)phenylalanine thus obtained was mixed together with 20 milligrams of 10 percent palladium on carbon catalyst and 10 milliliters of methanol and the mixture subjected to hydrogen at a pressure of 40 pounds per square inch for 3 hours. The catalyst was removed by filtration and the filtrate concentrated in vacuo to obtain 110 milligrams of a (S)-α-methylphenylalanine product as a crystalline solid. The product after recrystallization from methanol had a melting point of 307°–310° C. (dec). The product had the following optical rotation: $[\alpha]_{578} = 22.0$, c=0.1 and copper complex $[\alpha]_{546} = +180$, c=0.2. These are in good agreement with known value of (S)-α-methylphenylalanine prepared by conventional procedures: $[\alpha]_{578} = -22.8$, and copper complex $[\alpha]_{546} = +182.5$.

EXAMPLE 3

Preparation of Intermediate cis-3-Carbobenzyloxy-2-(2,4-dichlorophenyl)oxazolidinone In an operation similar to that described in the first step of Example 2, 2.13 grams of N-carbobenzyloxyalanine, 3 grams of 2,4-dichlorobenzaldehyde and 1.9 grams of p-toluenesulfonic acid hydrate and 30 milliliters of 1,1,1-trichloroethane were mixed and heated together. After refluxing for 8 hours with azeotropic removal of water, the mixture was allowed to cool to room temperature, diluted with methylene chloride, the methylene chloride solution washed with sodium bicarbonate solution, dried and the solvent evaporated off to obtain a residue.

The residue was stirred with saturated sodium bisulfite solution whereupon some precipitate and some gummy solid material formed. The solids were filtered, and slurried in methylene chloride whereupon some solid crystals formed. The latter was recovered by filtration, dissolved in methylene chloride, the methylene chloride solution washed with sodium bicarbonate solution, the washed solution dried, and the dried solution evaporated to obtain 3.3 grams of residue. The residue was determined by $C^{13}$ nuclear magnetic resonance (NMR) analysis to be a mixture of cis and trans isomers of 3-carbobenzyloxy-2-(2,4-dichlorophenyl)oxazolidinone compound in a ratio of cis:trans of 3.7:1. The crude material was chromatographed employing as eluant first, 1:1 hexane:methylene chloride and then methylene chloride alone to obtain 900 grams of cis-3-carbobenzyloxy-2-(2,4-dichlorophenyl)-oxazolidinone compound which after recrystallization from methylene chloride amounted to 500 milligrams of a purified oxazolidinone compound, m.p. 92°–94° C.

EXAMPLE 4

Preparation of Intermediate 4-benzyl-3-carbobenzyloxy-2-(2,4-dichlorophenyl)-4-methyl-oxazolidinone 740 milligrams (2 millimoles) of 3-carbobenzyloxy-2-(2,4-dichlorophenyl)oxazolidinone compound (prepared in a manner similar to that described in Example 3 from N-carbobenzyloxyalanine) was dissolved in 10 milliliters of tetrahydrofuran and the solution cooled to −78° C. 35 milliliters of 0.6 molar toluene solution of potassium hexamethyldisilazane was added dropwise with stirring to the cooled solution over a 5-minute period whereupon the solution turned yellow with the formation of the potassium enolate of the 3-carbobenzyloxy-2-(2,4-dichlorophenyl)oxazolidinone compound. After continuing the stirring at −78° C. for about five minutes to ensure completion of the reaction, 1 milliliter of benzyl bromide was added dropwise and the mixture stirred at −78° C. for thirty minutes, at 0° C. for thirty minutes and at ambient temperature for thirty minutes. Thereafter, water was added to the reaction mixture, the aqueous solution extracted with methylene chloride and the methylene chloride solution washed with dilute sodium chloride solution, dried, and the dried solution subjected to reduced pressure to vaporize the solvent and to obtain a residue. The latter was chromatographed employing first 1:2 methylene chloride:hexane then 1:1 methylene chloride:hexane to obtain 550 milligrams of a 4-benzyl-3-carbobenzyloxy-2-(2,4-dichlorophenyl)-oxazolidinone intermediate product. $C^{13}$ NMR showed this product to be a single compound. The product was crystallized from ether-hexane to obtain needles, m.p. 86°–88° C. in a yield of 300 milligrams. $[\alpha]_D = -149$, c=0.1 $CH_2Cl_2$.

EXAMPLE 5

Preparation of Intermediate cis-4-Benzyl-3-carbobenzyloxy-2-(2,4-dichlorophenyl)oxazolidinone from Schiff base A solution of 18.5 grams of 2,4-dichlorobenzaldehyde in 50 milliliters of ethanol was added to a solution of 16.5 grams of phenylalanine in about 50 milliliters of alcoholic sodium hydroxide (prepared from 4 grams of sodium hydroxide in 50 milliliters of 1:1 water:ethanol) to obtain sodium 2-(2,4-dichlorobenzalamino)-3-phenylpropionate (Schiff base) and water by-product in the reaction mixture. The solvent was evaporated and the residue was redissolved in ethanol and evaporatively distilled to remove the water in rotary evaporator. The vessel was flushed four times with 100 milliliter portions of toluene to obtain the Schiff base in a solid mixture.

To the crude mixture containing sodium 2-(2,4-dichlorobenzalamino)-3-phenylpropionate acid above described was added 150 milliliters of methylene chloride and 25 milliliters carbobenzyloxy chloride bromochloromethane and the resulting mixture stirred for four days. The mixture then was diluted with methylene chloride, the methylene chloride solution washed first with sodium bicarbonate solution, then with water, the washed methylene chloride solution was dried, and the dried solution evaporated to dryness to obtain a 4-benzyl-3-carbobenzyloxy-2-(2,4-dichlorophenyl)oxazolidinone compound as an oily residue. The oil was dissolved in a small volume of methylene chloride, and then precipitated with hexane while cooling. The crude product was chromatographed employing 1:1 methylene chloride:hexane as eluant to obtain 9 grams of a cis-4-benzyl-3-carbobenzyloxy-2-(2,4-dichlorophenyl)-oxazolidinone product which after crystallization first from ether plus hexane, and then from methylene chloride plus hexane amounted to 6 grams of a compound having a melting point of 109°–111° C. and $[\alpha]_D^{CH_2Cl_2} + 101.4$.

EXAMPLE 6

(R)-(α-Methyl)phenylalanine 400 milligrams of 4-benzyl-3-carbobenzyloxy-2-(2,4-dichlorophenyl)-4-methyloxazolidinone in which the methyl and 2,4-dichlorophenyl groups are in a cis relationship and the benzyl is in a trans relationship and prepared as described in Example 4 is dissolved in a mixture of 5 milliliters of methanol and 5 milliliters of 1N sodium hydroxide solution and the resulting solution is heated at reflux temperature for about 1 hour to obtain (R)-N-carbobenzyloxy (α-methyl)phenylalanine and benzaldehyde. The latter is removed by codistilling with water. The remaining solution is extracted with methylene chloride, the methylene chloride solution washed, dried and the solvent evaporated to obtain (R)-N-carbobenzyloxy-(α-methyl)-phenylalanine which is purified in a manner similar to that described in Example 2.

200 milligrams of the foregoing (R)-N-carbobenzyloxy-(α-methyl)phenylalanine is mixed together with 20 milligrams of 10 percent palladium on carbon catalyst and 10 milliliters of methanol and subjected to hydrogen pressure of 40 psi for 3 hours. The catalyst is then removed by filtration and the filtrate concentrated in vacuo to obtain a (R)-(α-methyl)phenylalanine product.

The product obtained by alkylation of (S)-alanine with benzyl bromide is an optical isomer of the product obtained in Example 2 by the alkylation of (S)-phenylalanine with methyl chloride.

EXAMPLE 7

In an operation carried out in a manner similar to that described in Examples 1 and 2, 22.5 grams (50 millimoles) of (S)-N,O-bis-(carbobenzyloxy)tyrosine, 70 milliliters (300 millimoles) of benzaldehyde and 9.5 grams (50 millimoles) of p-toluenesulfonic acid hydrate and about 200 milliliters of 1,1,1-trichloroethane are mixed together and heated in a water separator to azeotropically distill the water and to obtain cis and trans 3-carbobenzyloxy-4-[(4-carbobenzyloxyphenyl)methyl]-2-phenyloxazolidinone compounds in the mixture. The mixture is allowed to cool to ambient temperature and the intermediate oxazolidinone compounds recovered as residue. The residue is chromatographed on silica gel employing 1:1 hexane:methylene chloride in a manner similar to the method described in Example 1 to obtain cis 3-carbobenzyloxy-4-[(4-carbobenzyloxyphenyl)methyl]-2-phenyloxazolidinone.

1.6 grams (3 millimoles) of 3-carbobenzyloxy-4-[(4-carbobenzyloxyphenyl)methyl]-2-phenyloxazolidinone compound is dissolved in 30 milliliters of tetrahydrofuran and cooled to −78° C. To this solution is added 5 milliliters of 0.6M toluene solution of potassium hexamethyldisilazane with cooling. After about 5 minutes, 170 microliters (3 millimoles) of methyl iodide is added to the mixture and the mixture allowed to warm to 0° C. and maintained at the temperature for about one-half hour. The mixture is partitioned between pH 7 phosphate buffer and methylene chloride. The methylene chloride solution is washed, dried and concentrated in a manner similar to that previously described and then placed on silica gel and eluted, also in a manner similar to that previously described, to obtain a 3-carbobenzyloxy-4-[(4-carbobenzyloxyphenyl)methyl]-4-methyl-2-phenyl-oxazolidinone compound in which the (4-carbobenzyloxyphenyl)methyl and phenyl groups are in a cis relationship in the oxazolidinone ring.

400 milligrams of 3-carbobenzyloxy-4-[(4-carbobenzyloxyphenyl)methyl]-4-methyl-2-phenyloxazolidinone is dissolved in 5 milliliters of methanol and 5 milliliters of 1N sodium hydroxide and the resulting solution heated at reflux temperature for about one hour to obtain (S)-N-carbobenzyloxy-α-methyltyrosine compound. The hydrolysis mixture is heated with water to codistill benzaldehyde. The remaining solution is then extracted with methylene chloride, dried, and the dried solution concentrated to recover the tyrosine compound as residue.

200 milligrams of (S)-N-carbobenzyloxy-α-methyltyrosine is mixed together with 20 milligrams of 10 percent palladium on carbon catalyst and 10 milliliters of methanol and the mixture subjected to hydrogen at a pressure of 40 psi for several hours. Thereafter, the catalyst is removed and the filtrate concentrated to obtain a (S)-α-methyltyrosine product.

EXAMPLE 8

In operations carried out in a similar manner, the following compounds may be prepared:

(S)-3-Hydroxy-α-methyltyrosine from (S)-3-hydroxytyrosine by the reaction of (S)-N-carbobenzyloxy-3,4-bis(carbobenzyloxy)phenylalanine with benzaldehyde to obtain a cis-3-carbobenzyloxy-4-[(3,4-bis(carbobenzyloxyphenyl)methyl]-2-phenyloxazolidinone compound, methylating said oxazolidinone compound with methyl chloride to obtain a 3-carbobenzyloxy-4-[(3,4-bis(carbobenzyloxy)-phenyl)methyl]-4-methyl-2-phenyloxazolidinone compound, and thereafter subjecting it to alkaline hydrolysis followed by hydrogenolysis.

(S)-α-Ethylleucine from (S)-leucine by the reaction of (S)-N-carbobenzyloxyleucine with benzaldehyde to obtain a cis-3-carbobenzyloxy-4-isobutyl-2-phenyloxazolidinone compound, ethylating said oxazolidinone compound with ethyl chloride to obtain a 3-carbobenzyloxy-4-ethyl-4-isobutyl-2-phenyloxazolidinone compound, and thereafter subjecting it to alkaline hydrolysis followed by hydrogenolysis.

(S)-α-Isopropyllysine from (S)-lysine by the reaction of (S)-N,N-bis(carbobenzyloxy)lysine with benzaldehyde to obtain cis-3-carbobenzyloxy-4-(4-carbobenzyloxyaminobutyl)-2-phenyloxazolidinone compound, isopropylating said oxazolidinone compound with isopropyl bromide to obtain a 3-carbobenzyloxy-4-(4-carbobenzyloxyaminobutyl)-4-isopropyl-2-phenyloxazolidinone compound, and thereafter subjecting it to alkaline hydrolysis followed by hydrogenolysis.

In further similar operations, the following compounds are prepared.
(S)-α-Methylvaline
(S)-α-Methylisoleucine
(S)-α-Ethyltryptophane
(S)-α-Ethylornithine
(S)-α-Methylhydroxylysine.

What is claimed is:
1. A process for preparing an optically active acyclic or open chain α-alkyl-α-amino acid from the corresponding optically active acyclic α-amino acid which comprises:
   (1) converting an optically active acyclic α-amino acid to a 2-aryloxazolidinone compound in which the non-hydrogen substituent at the 4-position and the aryl group are in a cis relationship by:
     (a) reacting an optically active nitrogen protected α-amino acid with an aromatic aldehyde in the presence of an acid catalyst, or
     (b) reacting an optically active unprotected α-amino acid with an aromatic aldehyde in alkaline solution to produce a Schiff base of the amino acid salt and thereafter reacting the Schiff base with an acylating agent,

(2) stereospecifically alkylating said 2-aryloxazolidinone compound by first forming an alkali metal enolate by reacting the oxazolidinone compound with a strong base at greatly reduced temperatures followed by reacting the enolate with an alkylating agent, and (3) generating the α-alkyl-α-amino acid from the alkylated 2-aryloxazolidinone by alkaline hydrolysis to open the ring followed by hydrolytic or reductive removal of the protecting group.

2. A process for preparing an optically active acyclic or open chain α-alkyl-α-amino acid from the corresponding optically active acyclic α-amino acid which comprises:

(1) heating together a N-carbobenzyloxylated optically active acyclic α-amino acid and an aromatic aldehyde in the presence of a strong acid catalyst in an inert solvent with azeotropic removal of water by-product to obtain a mixture of cis and trans isomers of 2-aryl-3-carbobenzyloxyoxazolidinone intermediate, (2) separating the isomers to recover in substantially pure form cis-2-aryl-3-carbobenzyloxyoxazolidinone intermediate, (3) intimately contacting said oxazolidinone compound with a strong alkali metal base in an inert solvent medium at temperatures in the range $-70°$ to $-78°$ C. to obtain an alkali metal enolate of said oxazolidinone, (4) adding portionwise an alkylating agent to the cooled solution of the alkali metal enolate, then gradually allowing the temperature to rise to 0° C. to obtain a cis 4-alkyl-2-aryl-3-carbobenzyloxyoxazolidinone intermediate, (5) intimately contacting said 4-alkyl-2-aryl-3-carbobenzyloxyoxazolidinone with a dilute alcoholic solution of a base to obtain a cis α-alkyl-N-carbobenzyloxy acyclic α-amino acid, (6) subjecting an alcoholic solution of the cis α-alkyl-N-carbobenzyloxy acyclic α-amino acid to hydrogen at elevated pressures to reductively remove the carbobenzyloxy protecting group to obtain the desired α-alkyl-α-amino acid having the same enantiomeric configuration as that of the starting unalkylated α-amino acid.

3. A process according to claim 2 wherein the isomers are separated in Step 2 by applying the mixture of cis and trans/isomers to an adsorbent bed and eluting with an organic hydrocarbon solvent mixture.

* * * * *

UNITED STATES PATENT AND TRADEMARK OFFICE
CERTIFICATE OF CORRECTION

PATENT NO. : 4,508,921
DATED : April 2, 1985
INVENTOR(S) : Joseph S. Amato, Leonard M. Weinstock, Sandor Karady Page 1 of 2

It is certified that error appears in the above—identified patent and that said Letters Patent is hereby corrected as shown below:

In Column 2, lines 33-60, the flow diagram

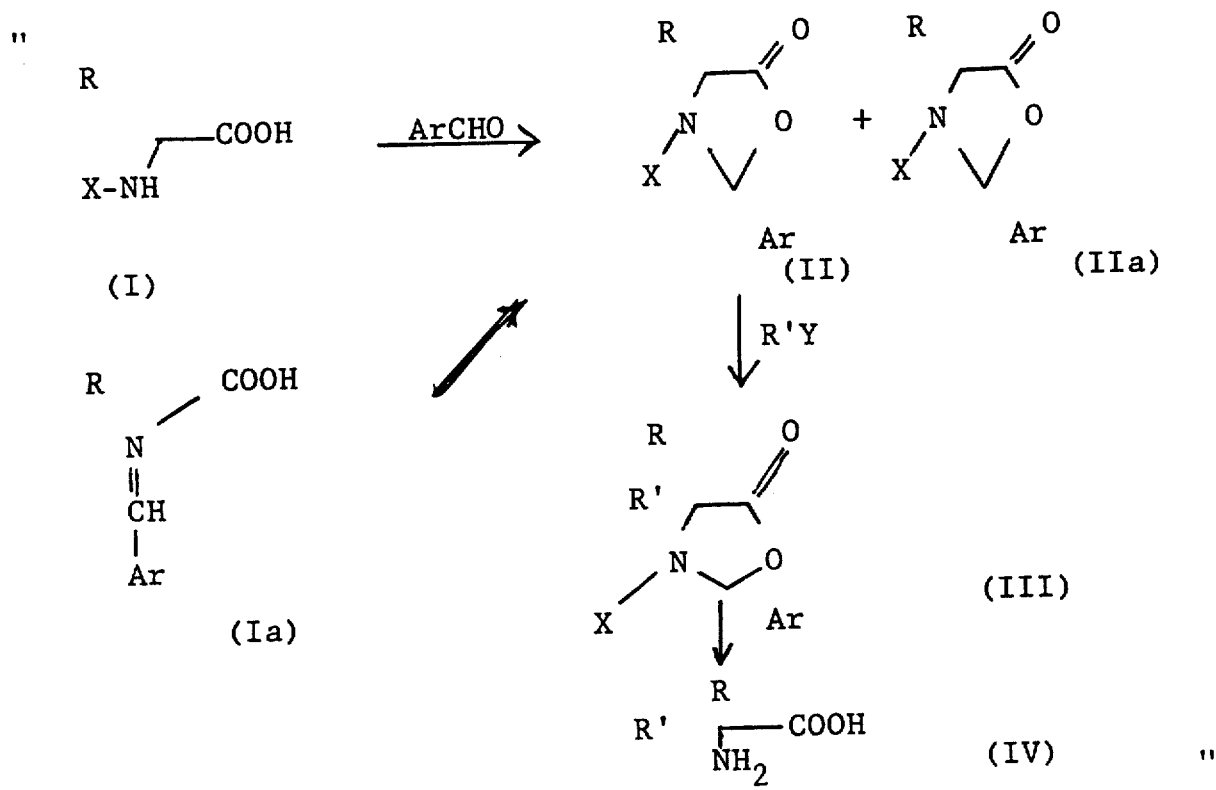

UNITED STATES PATENT AND TRADEMARK OFFICE
CERTIFICATE OF CORRECTION

PATENT NO. : 4,508,921
DATED : April 2, 1985
INVENTOR(S) : Joseph S. Amato, Leonard M. Weinstock, Sandor Karady It is certified that error appears in the above—identified patent and that said Letters Patent is hereby corrected as shown below:

Should read
--

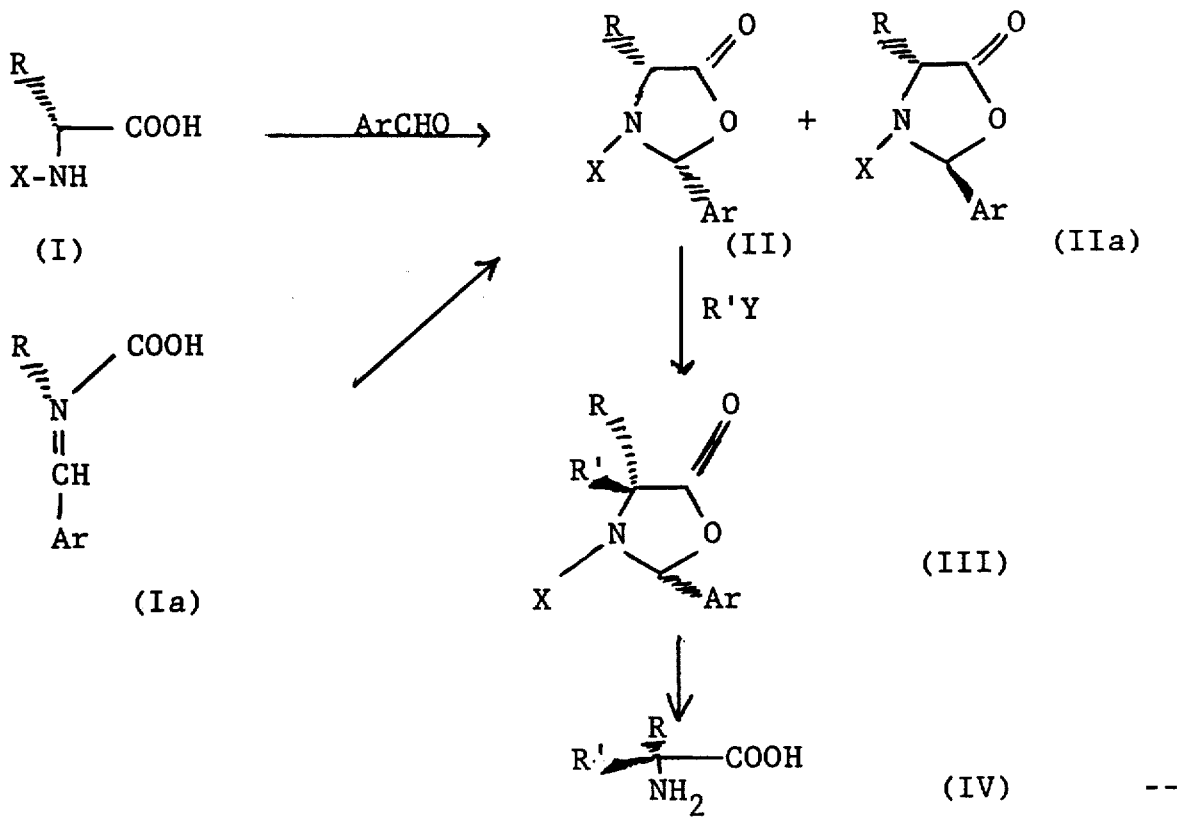

--

Signed and Sealed this

Twenty-second Day of October 1985

[SEAL]

Attest:

DONALD J. QUIGG

Attesting Officer

Commissioner of Patents and
Trademarks—Designate